United States Patent [19]

Firth et al.

[11] Patent Number: 5,616,134

[45] Date of Patent: *Apr. 1, 1997

[54] DISPOSABLE SELF-SHIELDING HYPODERMIC SYRINGE

[75] Inventors: John R. Firth, Portland, Oreg.; Anthony R. Perez, Alhambra; Ronald A. Meyer, San Dimas, both of Calif.

[73] Assignee: Safety Syringes, Inc., Arcadia, Calif.

[ * ] Notice: The portion of the term of this patent subsequent to Sep. 14, 2013, has been disclaimed.

[21] Appl. No.: 875,032

[22] Filed: Apr. 28, 1992

Related U.S. Application Data

[63] Continuation of Ser. No. 581;734, Sep. 12, 1990, Pat. No. 5,108,378, which is a continuation-in-part of Ser. No. 521,243, May 9, 1990, abandoned.

[51] Int. Cl.$^6$ ............................................. A61M 5/32
[52] U.S. Cl. ........................... 604/192; 604/198; 604/263
[58] Field of Search .................................. 604/192, 198, 604/263, 187, 110

[56] References Cited

U.S. PATENT DOCUMENTS

| | | | |
|---|---|---|---|
| 1,921,034 | 8/1933 | La Marche | 604/198 X |
| 2,571,653 | 10/1951 | Bastien | 604/198 |
| 4,747,831 | 5/1988 | Kulli | 604/198 |

*Primary Examiner*—John D. Yasko
*Attorney, Agent, or Firm*—Lyon & Lyon

[57] ABSTRACT

The disclosure relates to a hypodermic syringe which is stackable, disposable and non-reusable with features to prevent users from accidentally stabbing themselves before or after use; insert the needle with preferred orientation: render is unusable after use; measure precise amounts of injected or withdrawn fluid and retract the needle with one finger after use.

11 Claims, 4 Drawing Sheets

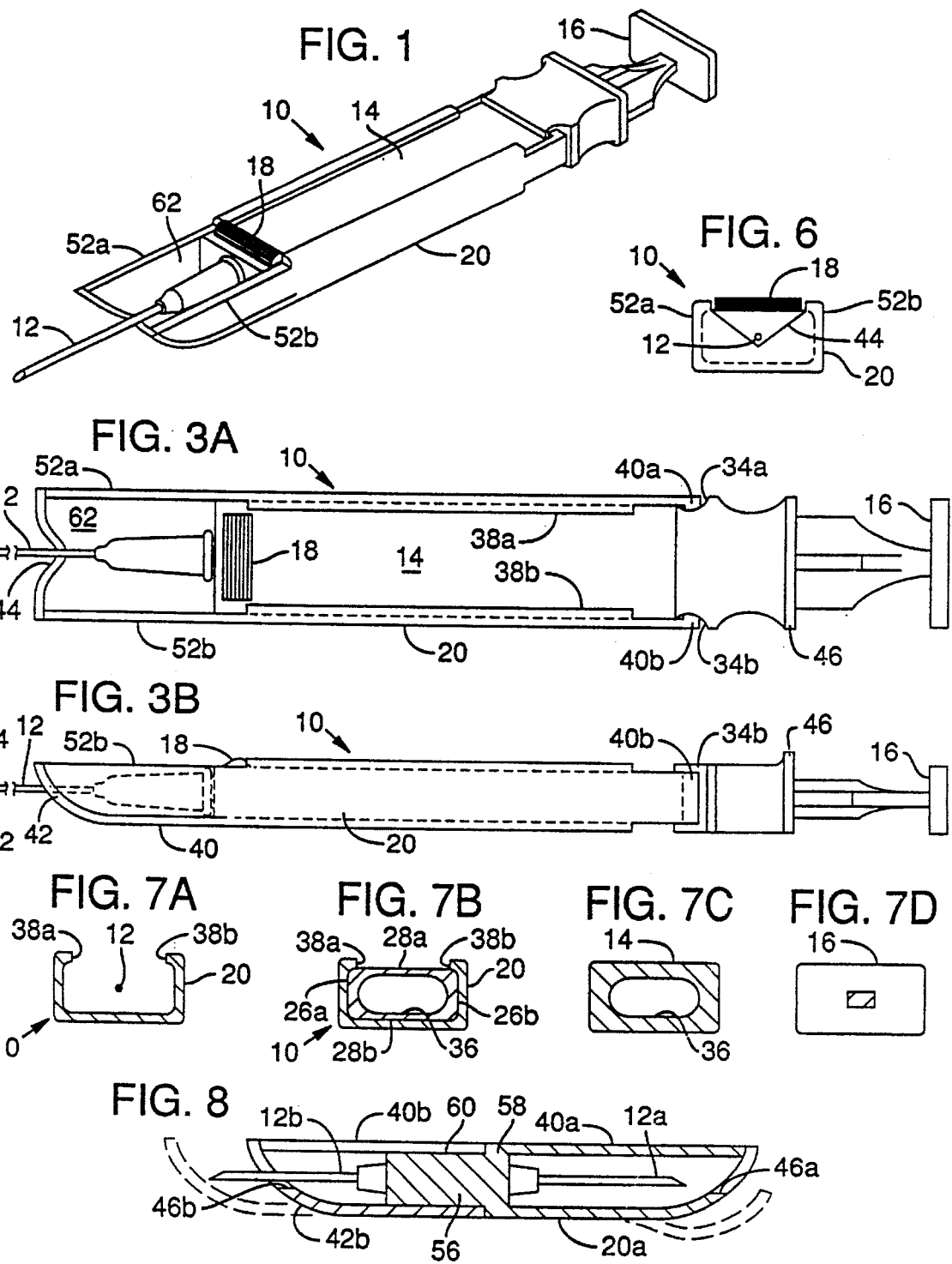

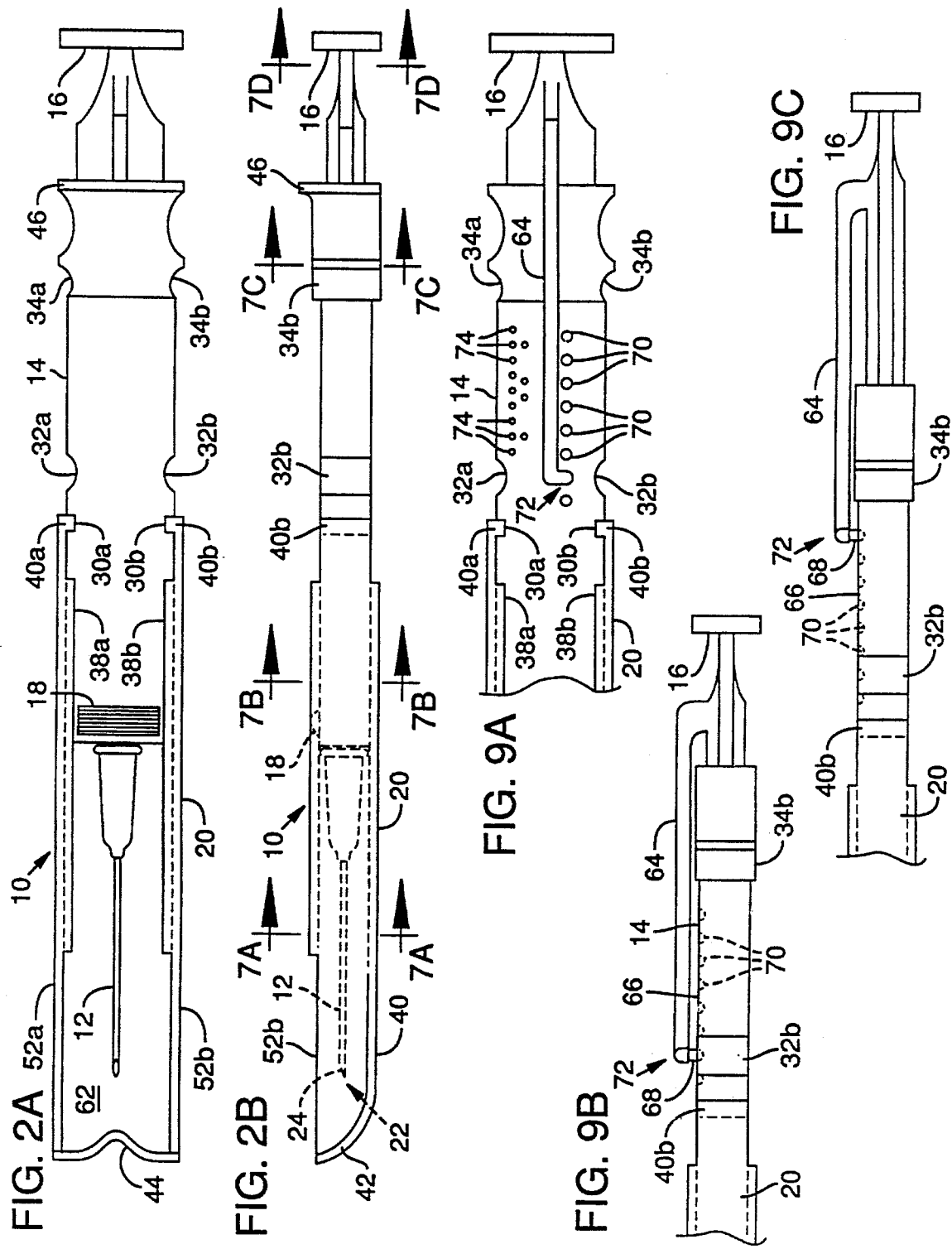

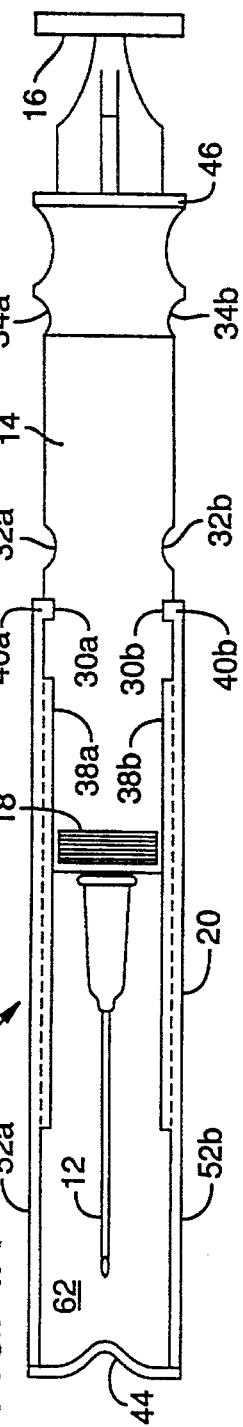
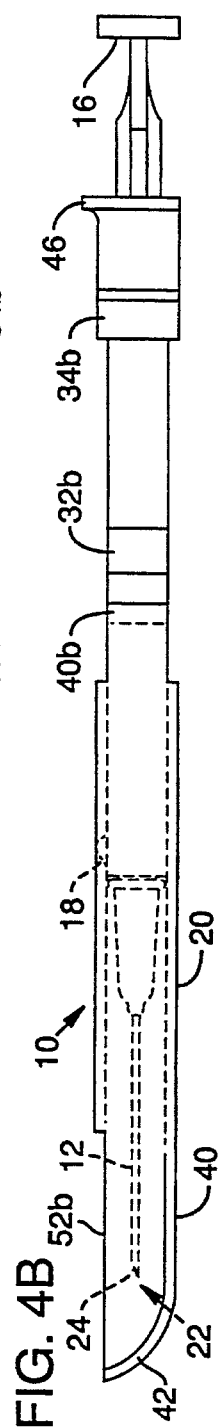
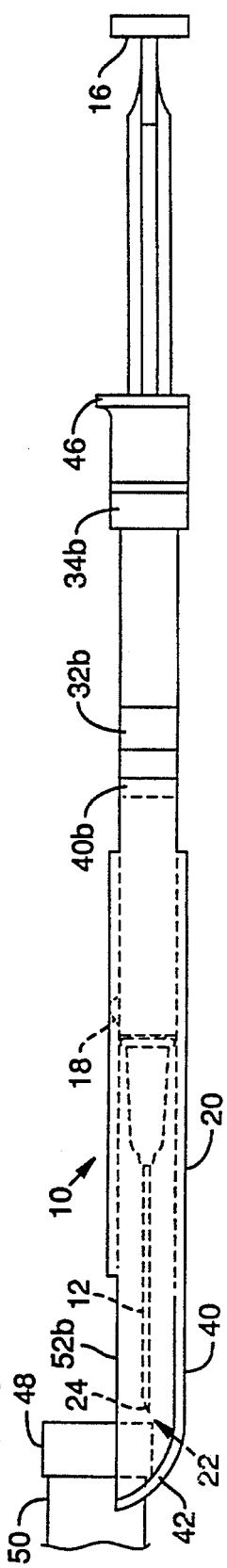
FIG. 4A  FIG. 4B  FIG. 5A  FIG. 5B

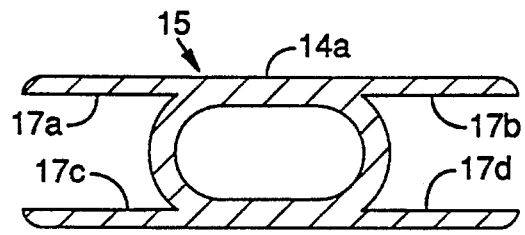
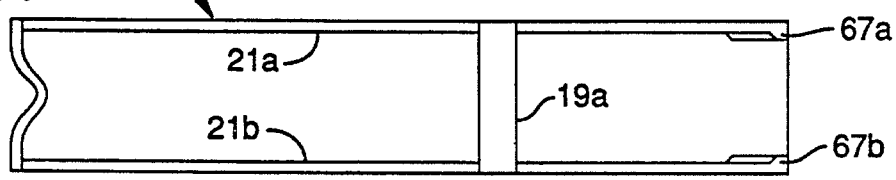
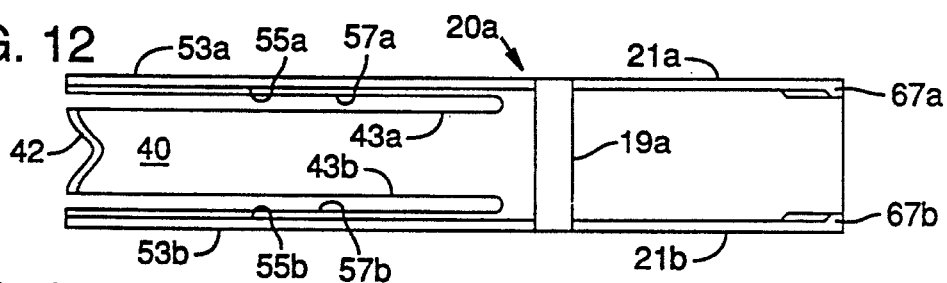
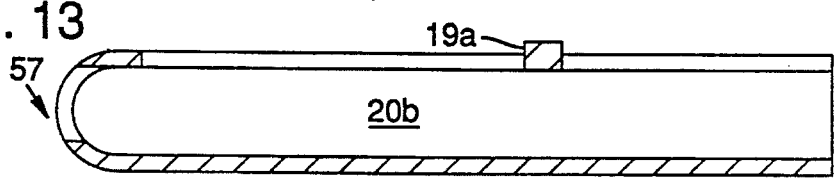
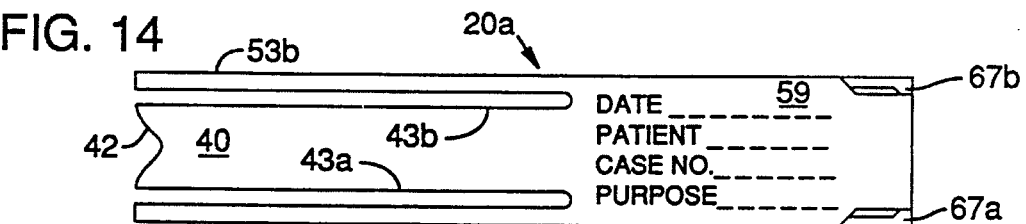
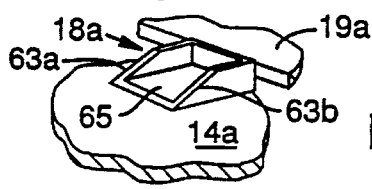
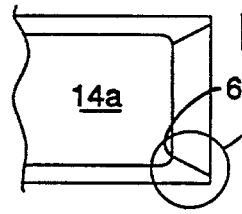
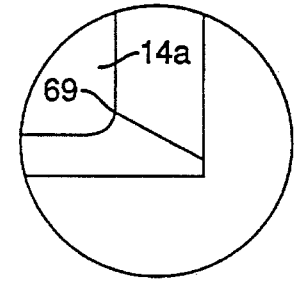
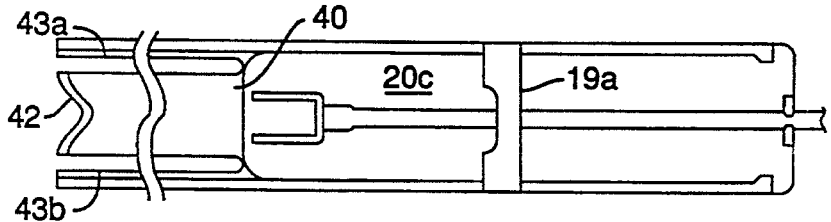

5,616,134

DISPOSABLE SELF-SHIELDING HYPODERMIC SYRINGE

This is a CONTINUATION of application Ser. No. 07/581,734, filed Sep. 12, 1990, and to be issued Apr. 28, 1992 as U.S. Pat. No. 5,108,378, which was a CONTINUATION-IN-PART of application Ser. No. 07/521,243, filed May 9, 1990 by two of the applicants therein and now abandoned.

INTRODUCTION

The present invention is, in general, an improved hypodermic syringe and, in particular, a stackable, disposable, non-reusable, hypodermic syringe with features to:

prevent users or patients from accidentally stabbing themselves before or after use;

insert the needle with preferred orientation;

render it unusable after use;

measure precisely amounts of injected or withdrawn fluid; and retract the needle with one finger after use.

Some of the foregoing features are available in a double-needle embodiment.

BACKGROUND OF THE INVENTION

The development of safe medical syringes and procedures for using them have long been a matter of concern, especially to the medical field. Many medical procedures, such as the transfusion of blood and the administration of insulin in some circumstances, require the use of needles and syringes, with their attendant hazard of accidental scratch or puncture. Recently, the risk has increased dramatically of contracting virulent and fatal or near-fatal infections during legitimate medical procedures using needles, and the general public as well as the medical profession has demanded safer products and procedures.

Efforts to minimize the risk of accidental infection have been made for several decades. Some representative efforts are:

La Marche U.S. Pat. No. 1,921,034 discloses a protector case for a syringe of conventional type, which allows for the needle to be exposed the correct amount for the type of shot to be given, and to be retracted after use to protect others from being accidentally punctured thereby.

Bastien U.S. Pat. No. 2,571,653 discloses a syringe body encased in a slidable protector case, having built-in detents to hold the needle in a retracted position prior to and following use, while permitting the needle to be exposed the correct length for the purpose.

Tschischeck U.S. Pat. No. 2,586,581 discloses an add-on magnifying attachment for syringes. It has no relevance to the present invention, except to disclose one means of making the scale more readable and the dosage more accurate.

Norgren U.S. Pat. No. 3,943,927 discloses an injection device to be carried by persons having allergic reactions to insect or snake bites, or bee stings, where antitoxins or other emergency remedies need to be administered immediately under conditions of great physical or emotional stress. It has little relevance to the present invention.

Ethington U.S. Pat. No. 4,018,223 discloses a tactile-detent dosage metering device for use by persons with impaired vision.

Chen U.S. Pat. No. 4,728,321 discloses a means to render a needle unfit for further use, by placing thereon a syringe cap and permanently cementing it in place.

Bogan U.S. Pat. No. 4,738,663 discloses a removable protective cover for the needle of a syringe.

Leopoldi et al U.S. Pat. No. 4,743,234 discloses a syringe with needle shield which provides protection to users when the shield is moved to cover the needle. The mechanism provides detent positions in both extended and retracted positions, but not a permanently locked position.

None of the above references disclose, either singly or in combination, the structure and attendant features of the present invention.

BRIEF DESCRIPTION OF THE PRESENT INVENTION

The basic invention is a combination hypodermic syringe/protector case, which consists of four principal parts:

1. needle
2. body;
2. plunger (and plunger seal); and
3. protector case.

The body of the hypodermic syringe has a rectangular, rather than the traditional circular, cross-section, allowing greater packaging density.

The plunger (and the bore) can have the traditional circular cross-section or, preferably, any non-circular shape, including rectangular or oval, which latter have several advantages, as enumerated hereinafter.

The rectangular cross-section permits encasing the syringe in a simple U-shaped channel, which acts as a protector case and slide, in which the syringe body can slide either way to reach one of its several physical states. If the plunger has an oval or flat rectangular cross-section, the thickness of the combined syringe and protector case is substantially the same as that of a syringe of the same capacity or volume, but with a conventional structure. The protector case preferably includes inwardly pressing fingers which, mating with shallow grooves formed into the sides of the syringe body, form detent mechanisms, described more completely hereinafter. The protector case also includes a shaped cut-out, in a flexible section, which acts as a shield to protect persons from the needle point both before and after use. These features are described in more detail hereinafter.

Before use, the syringe body is withdrawn from its functional position, and is held in place by a first detent mechanism, so that the needle is protected by a shield incoporated into the protector case.

If desired, the needle can have thereon a removable shield of conventional design, fabricated of a shrinkable material such that the application of heat, microwave, chemical or other energy will shrink the shield into intimate contact with the needle. Further, the protector case itself can also have thereon an appropriately shaped removable shield fitting over the needle end thereof, of the same shrinkable material as the needle shield. After use, the shield(s) can be replaced on the protector case and/or the needle, carried to a point of central disposal, and treated with heat, microwaves, chemicals or other processes that will shrink them into intimate contact with the needle, rendering it unusable thereafter.

Alternatively, when the protector case is withdrawn to its permanent position, and is no longer to be used, a block of shrinkable or meltable material can be inserted into the cavity between the sides of the protector case, over the whole length of the needle, which then can be shrunk or melted into an amorphous mass over the needle, rendering it unfit and unavailable for further use.

To prepare the syringe for use, the needle and protector case shields are removed, if present. The syringe body is slid forward from its storage position within the protector case to a position as determined by a second detent mechanism, exposing the correct length of needle for desired insertion depth.

When the injection has been completed or the blood has been drawn, the needle is withdrawn by retracting the syringe to a third, permanent position, where it is held in place by a third detent mechanism from which it cannot be moved without intent and only with considerable difficulty.

To transfer drawn blood or serum from the syringe, a conventional stoppered specimen tube is positioned in the shaped end of the protector case, with the stopper thereof adjacent to the needle tip. The tube is pressed transversely to the syringe body, forcing the flexible section of the protector case out of the way and permitting the stopper of the specimen tube to be forced onto the needle and the contents of the syringe emptied into the tube. This can be repeated as often as necessary, depending upon the number of specimens needed.

It is recognized by nurses and others who give shots regularly that a desired orientation of the needle when inserting it into a patient is with the tapered portion of the tip upwards, so that the depth of insertion can be gauged with respect to the needle opening and a blood vessel, for example. The rectangular shape makes it possible, during production, to automatically orient the needle with respect to the upper face of the syringe, so that the needle can be efficiently inserted, particularly under difficult light conditions, or with a struggling patient.

The benefits of the present invention are several:
1. the protector case provides protection from accidental injury both before and after use, and during transfer of fluids to specimen tubes;
2. the detent mechanism provides positive positioning of the syringe prior to, during, and after use;
3. the rectangular structure has several advantages:
   a. close packing of multiple numbers during shipping and storage;
   b. automatic positioning of the needle with respect the syringe body; and thus
   c. convenient positioning of the needle for most effective insertion thereof into a patient;
   d. prevention of needle re-use by shrinkable shields or meltable blocks of material;
4. the rectangular or oval shape of the plunger and internal cavity makes it easier to find and read the dosage markings.

Other features can be added to the above basic invention which give additional advantages:
5. the plunger can have attached thereto an extension, parallel to and extending toward the needle, with tactile detent features or markings thereon, indicating the volume of fluid expelled, for use in giving metered doses in situations where vision is impaired (in a darkened room, for example);
   a. sight-impaired persons with diabetes, for example, would benefit by the use of such an instrument;
6. the syringe body can have a raised ridge on the needle end, so that the user can hold the syringe between thumb and middle finger and retract the syringe with the forefinger;
7. the protective case feature can be incorporated in a double-needle fixture, for use when multiple samples of a patient's blood, are to be obtained at the same time. A nurse or other medical person is at a substantial risk using a fixture of conventional design in this situation. With an unprotected-needle fixture, one hand must be occupied in holding the first needle in a patient's arm while the other hand must withdraw one container from the second needle and reinsert another thereon, perhaps several times, leaving the needle exposed each time. Or, even a fixture with a protected needle requires that the collecting container be screwed onto the fixture, requiring precise manipulation in an awkward situation. With the present invention, the needle is covered by the protective case while one container is easily exchanged for another.

To recap, the important features are:
1. rectangular shape of syringe and internal bore;
2. protector case which keeps needle protected during storage, after use, and during transfer of fluid to specimen tubes;
3. shields of shrinkable or meltable material to render needle unreusable;
4. first, second and third detent mechanisms for positive positioning of syringe and needle with respect to protector case, before during and after use;
5. orientation of needle with respect to rectangular case to facilitate use in difficult situations; and
6. tactile detent metered dosage mechanism for use by persons with impaired vision or in dimly lighted situations.

The improvements in this CIP application are:
1. an improved cross-sectional shape of the syringe body, reducing shrinkage and/or warpage due to non-uniform thickness of material;
2. an improved structure to the shield or protector case, including:
   a. a stronger structure with less possibility of twisting and/or warpage;
   b. an improved shape to the nose thereof in one embodiment; and
   c. an improved structure for the flexible nose portion of the original embodiment;
3. an improved finger-boss structure for the one-finger withdrawal feature;
4. an improved and simplified detent mechanism;
5. a convenient means of applying identifying indicia to the syringe body;
6. an improved structure for the blood collection embodiment;
7. an improved structure to prevent withdrawing the plunger from the syringe body.

BRIEF DESCRIPTION OF THE DRAWINGS

FIG. 1 is an oblique isometric view of the present invention, disclosing the interrelationship of the various parts.

FIGS. 2A and 2B are plan and profile views, respectively, of the syringe in its storage state before use.

FIGS. 3A and 3B are plan and profile views, respectively, of the syringe in its extended state, ready for use.

FIGS. 4A and 4B are plan and profile views, respectively, of the syringe in its retracted state, following use.

FIGS. 5A and 5B are plan views of the syringe prior to, and during, insertion of the needle into a storage tube, respectively, for transfer of the fluid contents thereof.

FIG. 6 is a view of the syringe from the needle end thereof.

FIGS. 7A–D discloses cross-sectional shapes of the syringe at sections A—D of FIG. 2B, transverse to the longitudinal axis thereof.

FIG. 8 discloses a double-needle fixture incorporating some of features of the present invention.

FIG. 9 discloses a tactile detent mechanism enabling use of the present invention in dim light or by those with vision impairment.

FIGS. 10–17 relate to the improvements disclosed in this present CIP application.

FIG. 10 discloses the improved shape of the syringe body in cross-section.

FIG. 11 discloses the improved syringe protector case structure.

FIG. 12 discloses the improved structure of the flexible nose of the syringe protector case.

FIG. 13 discloses a second embodiment of the nose shape of the syringe protector case.

FIG. 14 discloses the improved syringe protector case providing a data recording area.

FIG. 15 discloses the improved finger-boss permitting one finger withdrawal of the syringe.

FIG. 16 discloses an improved structure for the detent mechanism.

FIG. 17 discloses the improved structure of the blood collection embodiment of the syringe.

FIG. 18 discloses an improved structure of the syringe body to prevent accidental removal of the plunger from the body.

DETAILED DESCRIPTION OF THE PRESENT INVENTION

Turning now to FIG. 1, we see the syringe of present invention 10, including needle 12, body 14, plunger 16, seal 18, and protector case 20.

Needle 12 is preferably a standard needle of diameter and length appropriate to the desired use, although the benefits of the invention may be realized with a needle of nearly any configuration. To obtain the benefits of needle orientation, as explained hereinafter, needle 12 preferably has thereon beveled point 22, with beveled portion 24 being all on one side thereof. It is preferably affixed to body 14 by a standard press fit, such as is well known in the art, although it could be permanently affixed thereto, or have bayonet or screw attachment means, if the use so dictated.

Body 14 preferably has a shape substantially rectangular in cross-section, as disclosed more clearly in FIG. 6A, although it could have an oval or other flattened shape to obtain the benefits enumerated hereinafter. The rectangular shape has two short sides 26a and 26b, and two long sides 28a and 28b, thereon. Body 14 has formed therein, preferably into short sides 26a and 26b thereof, three pairs of grooves, 30a and 30b, 32a and 32b, and 34a and 34b, whose function is explained hereinafter. Grooves 30a and 30b have straight sides thereto, while grooves 32a and 32b, and 34a and 34b, are shallow, with sloping sides thereto, as disclosed more clearly in FIG. 2. Bore 36 of body 14 preferably has a shape rectangular in cross-section, to obtain the benefits described hereinafter, although it could be round or, in this case, preferably oval.

Plunger 16 is of a substantially standard structure, except that it has a cross-sectional shape to match that of bore 36, that is, greater in breadth than in height, and preferably rectangular in cross-section. Plunger 16 also has thereon a seal 18 of a resilient material, to prevent any leakage of contained fluid during use of syringe 10.

Protector case 20 contains therein several features which permits the attainment of several of the benefits of the present invention. It fits snugly but slidably around the external surface of body 12. To permit the insertion of a deformable block of material around the needle and realize the benefit of rendering the syringe unusable, case 20 preferably has a U-shape thereto, with an open space above the needle. This is disclosed most clearly in FIGS. 7A and 7B, including lips 38a and 38b thereon extending over the edge of body 12 to keep it snugly within case 20. The external shape of case 20 is preferably substantially rectangular in cross-section, to permit stacking and realize the benefits thereof for shipping and storing before use, but it could be oval or elliptical and accomplish most of the same purposes. The internal shape of case 20 is complementary to the external shape of body 12. Case 20 has inwardly projecting fingers 40a and 40b which, in cooperation with grooves 30a and 30b, 32a and 32b, and 34a and 34b, forms a detent means and, in cooperation therewith, defines third, first and second positions of body 14 within case 20, respectively.

Case 20 further includes flexible section 40, extending beyond point 22 when syringe 10 is in first and third detent position, providing protection from needle point 22, as explained hereinafter. Flexible section 40 includes upwardly curving portion 42, which has in the end thereof wide V-shaped notch 44. Finally, case 20 includes friction means 46, which could be a simple ridge across the end of case 20, as shown in FIGS. 1B, 2B, 3B, 4A and 4B, to exert pressure thereon by a finger.

OPERATION OF THE PRESENT INVENTION

The operation and novel features of syringe 10 will now be explained.

As described hereinbefore, syringe body 14 preferably has an external cross-section which is substantially rectangular in shape, to match the internal cross-section of protector case 20. Body 14 movably slides within protector case 20. When a user selects syringe 10 from a quantity thereof, body 14 will be in first position, as defined by inwardly extending fingers 40a and 40b, resting in grooves 32a and 32b, respectively. Needle 12 will be affixed to body 14 by needle placement equipment (not shown) so that beveled portion 24 of needle 12 will be facing toward the open space between inwardly extending fingers 38a and 38b, for a purpose described hereinafter. The beveled portion can also be oriented toward one of the other sides of the syringe, if desired.

To illustrate the benefits of syringe 10, assume that it will be used for withdrawing blood from a patient, and transferring it to sealed containers such as stoppered test tubes for testing and/or further processing.

To use the syringe, body 14 will be pushed toward its second position, so that needle 12 will be extend through V-shaped notch 44. Body 12 will come to rest when inwardly extending fingers 40a and 40b slide into notches 34a and 34b, respectively. The sloping sides of notches 32a and 32b, and 34a and 34b, permit inwardly extending fingers 40a and 40b to easily slide out of and into said notches, while providing a distinct "detent" feel for users, so that they know when needle 12 has been extended the desired amount for proper insertion into a vein. As anyone knows who has given shots, inserting a needle into a vein can be done with much greater accuracy when beveled portion 24 is facing upward, so that the point and the hole in the needle can be seen. Because the pre-use placement of needle 12 gives it the desired orientation, the user does not need to rotate it to insure accurate placement thereof. For some purposes, e.g., inserting a needle into the side of a vein, other orientations may be preferred, however, and proper placement of the needle will be facilitated by the substantially rectangular shape.

As needle 12 is inserted into the vein, upwardly sloping portion 42 both encourages the correct angle of insertion, and prevents needle 12 from being inserted too deeply, as portion 42 will come to rest against the patient's skin at the correct depth of penetration.

When plunger 16 has been withdrawn so as to obtain the desired amount of blood in body 14, the user preferably holds body 14 with the thumb and middle finger of one hand, places the forefinger on ridge (or friction means) 46 and, by finger pressure thereon, withdraws body 14 from case 20. When body 14 has been withdrawn to post-use position three, inwardly extending fingers 40a and 40b snap into straight-sided groove 30a and 30b, respectively. While body 14 is being moved to position three, needle 12 is also being withdrawn from the patient, with the sterile surface of upwardly curving portion 42 providing resistance for tender or fragile skin against the withdrawing needle.

Although detent fingers 40a and 40b easily slide across the sloping sides of grooves 32a and 32b, the immovable fit of fingers 40a and 40b in straight-sided grooves 30a and 30b, respectively, prevent the movement of syringe body 14 from position three without the destruction of protector case 20. This feature provides much desired and needed protection against accidental stab wounds by unprotected needles during handling thereof after removal from the patient.

The transfer of blood from syringe 10 to other containers for further processing or testing can now take place easily and safely with the aid of flexible section 40 and upwardly curving section 42 thereof. As disclosed in FIG. 4A, stopper 48 of container 50 is a standard stopper of rubber or other resilient material which can be pierced easily by a needle and yet prevent external contamination. Container 50 is placed in V-shaped notch 44, and pressed transversely to the axis of case 20 and needle 12. Because of the flexible nature of flexible portion 40, it moved aside, allowing stopper 48 to be brought into line with needle 12. Stopper 48 is then pushed against needle 12 by longitudinal pressure on container 50, and is pierced thereby, enabling a desired quantity of blood to be transferred into container 50 by pressure on plunger 16. This procedure can be repeated as often as required, until the requisite number of samples have been obtained. It will be seen immediately by those skilled in the art that this procedure is more convenient than present procedures, and is substantially safer, especially where several samples have to be withdrawn from the same syringe. Extended fingers 52, which are not connected to flexible portion 40, provide substantial protection against accidental stabbing, either of self or other nearby parties, by the holder.

This feature of protector case 20 is adaptable to a double-ended needle fixture 54, as disclosed in FIG. 8.

Body 56 is encased in protector case 20a, which has some of the same features of protector case 20, as described hereinbefore, but with certain changes to facilitate usage in drawing multiple samples sequentially. Body 56 has first end 58 and second end 60, with needles 12a and 12b thereon, respectively. Protector case 20a includes extended portion 40a, which is fixedly attached to first end 58 of body 56, and extended portion 40b, which slides on second end 60. Each of extended portion 40a and 40b has upwardly curving portion 42a and 42b thereon, respectively, with V-shaped notches 46a and 46b therein, again respectively.

In this case, extended portion 40b slides on second end 60 of body 56, to permit insertion of needle 12b into a patient. Portion 40a extends permanently beyond the end of needle 12a, however, to give protected but convenient access thereto, as described hereinbefore, when obtaining multiple specimens from one patient.

Both syringe embodiment 10 and fixture embodiment 54 can easily be made unusable. Block 62 of deformable material is pressed between extending fingers 48 of the protector case, and some form of external energy, such as heat or microwave energy, is applied thereto, melting and otherwise deforming block 62 around the needle and the end of body 14, rendering syringe 10 unfit for further use.

FIG. 9 discloses a tactile indicator for use by those with vision impairment or in inadequate light. Plunger 16 has affixed thereto extension 64, which extends along exposed external surface 66 of syringe body 14, between edges 38a and 38b. Extension 64 also has on the tip thereof, nob 68 which mates with depressions 70, impressed into surface 66 of body 14, forming tactile and/or aural detents 72. As the plunger was depressed, the feel or sound of detents 72 would indicate to one experienced in the use thereof the quantity of fluid injected. Surface 66 also could have formed thereon raised symbols 72, for example, Braille symbols. Detents 72 also could be formed by other means than knobs and depressions.

BRIEF DESCRIPTION OF THE FEATURES OF THE IMPROVED SYRINGE

Briefly, the improvements over the parent application which are the subject of this Continuation-In-Part application relate to:

1. an improved cross-sectional shape of the syringe body, reducing shrinkage and/or warpage due to uneven thickness of material (FIG. 10);
2. an improved structure to the shield or protector case, including:
   a. a stronger structure with less possibility of twisting and/or warpage (FIG. 11);
   b. an improved structure for the flexible nose portion of the original embodiment (FIG. 12);
   c. an improved shape to the nose thereof in second embodiment (FIG. 13);
3. a convenient means of applying identifying indicia to the syringe body (FIG. 14);
4. an improved structure for the one-finger withdrawal feature (FIG. 15);
5. an improved structure for the detent mechanism (FIG. 16);
6. an improved structure for the blood collection embodiment (FIG. 17); and
7. an improved structure to prevent accidental withdrawal of the plunger from the syringe body (FIG. 18).

Turning now to FIGS. 10–17, we see disclosed in greater detail the improvements which are the subject of this Continuation-In-Part application.

FIG. 10 discloses one embodiment of the improved external shape in cross-section of improved syringe body 14A, which is molded of any of several well-known plastics used in medical products. This embodiment is a horizontal H-shape 15, having extensions 17A–17D extending tangentially outward from the surface of syringe body 14A so that the extremities thereof define a shape conforming to the shaped internal configuration of syringe protector case 20A, which is disclosed here as having a basic horizontal rectangular shape. However, body 14A could have any of a number of external shapes which lend themselves to the requirements of the present invention. For example, extensions 17A–17D could extend radially from body 14A in a flattened X-shape and still remain within the spirit and intent of the improvement, which is to inhibit dimensional shrinkage and distortion of the plastic material by providing an substantially uniform thickness of plastic throughout the cross-sectional shape, and providing a uniform sliding friction between plunger 16 and body 14A, and between body 14A and syringe shield or protector case 20A.

FIGS. 11–13 disclose, in longitudinal-section, improved protector case 20A, with several improved features therein giving important advantages over the existing case structure 20:

1. cross-member 19A gives greater lateral support to side-members 21A and 21B. Member 19A, by engaging improved friction means, or finger-engaging boss 18A on the nose-end of body 14A, provides:
    a. a uniform stop in the "USED" position of syringe 10, with needle 12 wholly retracted behind protective case 20A, preventing protector case 20A from further travel toward needle end of body 10 (FIG. 11);

2. improved nose structure 41A, in which forwardly extending side fingers 53A and 53B are separated from flexible section 40, having upwardly-curved portion 42, by slots 43A and 43B. By locating slots 43A and 43B inwardly from inner surfaces 55A and 55B of fingers 53A and 53B, lips 57A and 57B are formed, giving greater lateral support to fingers 53A and 53B (FIG. 12);

3. improved nose shape 57 to protector case 20B provides an embodiment which has certain advantages over the original embodiment with upwardly curving portion 42, as hereinafter discussed more fully (FIG. 13).

FIG. 14 discloses data recording area 59 which can be formed on protector case 20A or 20B, or other configurations thereof, giving easy and convenient means of recording data appropriate to a particular use or patient directly on the syringe involved.

FIG. 15 discloses boss 61, which provides certain advantages over friction means 18 for the one-finger withdrawal feature. Boss 61 includes, on the nose end thereof, ramps 63a and 63b forming finger stall 65 therebetween. Boss 61 is shaped to permit cross-member 19A to slide over boss 61 during assembly, yet provides a positive stop to prevent removal of protector case 20A without difficulty. Finger stall 65 provides a positive grip to facilitate removal of syringe body 14A and needle 12 into protector case 20A.

FIG. 16 discloses an improved structure of inwardly directed fingers 67A and 67B of the detent permitting a substantial decrease in mold complexity and therefore a decreased cost of manufacture.

FIG. 17 discloses an improved structure for the blood collection embodiment, giving much greater protection to the user. Use of the flexible section 40 permits blood or other fluids to be transferred to one or more receptacles as the occasion requires, without exposing the handler to the contaminated needle.

FIG. 18 discloses an improved structure to the internal bore of the syringe body, with lip 69 preventing accidental withdrawal of plunger 16 from syringe body 14A.

The fixed nose and flexible nose embodiments of the protector case can be combined with the blood collection or the blood transfer embodiments, and the data recording feature can be applied to any of these combinations. The improved detent mechanisms and finger boss can be combined with the other combinations in any appropriate manner.

The terms and expressions which have been employed in the foregoing specification are used therein as terms of description and not of limitation, and there is no intention, in the use of such terms and expressions, of excluding equivalents of the features shown and described, or portions thereof, it being recognized that the scope of the invention is defined and limited only by the claims which follow.

What we claim as our invention is:

1. A medical fixture for collecting, holding and transferring fluid, including a needle, a body, and a protector case, wherein:
    I. said body has:
        A. a first end and a second end;
        B. a needle mounted on said first end;
    II. said protector case slidably contains said body,
    THE IMPROVEMENT COMPRISING:
        a. said body and said protector case mutually incorporating first and second detent means for holding said body within said protector case, in first and second positions, respectively, whereby:
            1. said needle is:
                A. extended for use in said first position; and
                B. immovably retracted and wholly contained within said protector case in said second position;
        b. said body having:
            1. an external first rectangular cross-section thereto;
        c. said protector case having:
            1. an external second rectangular cross-section;
            2. an internal third rectangular cross-section, complementary to said external first rectangular cross-section; and
            3. a flexible section providing access to said needle in said first position.

2. The syringe of claim 1, wherein said external first rectangular cross-section is defined by extremities extending from said body.

3. The syringe of claim 1, wherein said external first rectangular cross-section is defined by extremities extending substantially tangentially from said body.

4. The syringe of claim 1, wherein said external first rectangular cross-section is defined by extremities extending substantially radially from said body.

5. The syringe of claim 1, wherein said body has on a lower surface thereof opposite said upper surface a data recording area.

6. The syringe of claim 5, wherein two side members of said protector case each have thereon at said second end inwardly extending fingers respectively engaging two shaped grooves on said body, and forming detents therein.

7. The syringe of claim 1, wherein said first end of said bottom of said protector case has a flexible section separated from two side members by two longitudinally extending slots, said two side members having longitudinal lips thereon.

8. The syringe of claim 7, wherein said two side members of said protector case each have thereon at said breech end inwardly extending fingers respectively engaging shaped grooves on said body, and forming detents thereby.

9. The syringe of claim 1, wherein said first end of said protector case has an end member thereon extending between said two side members, said end member having therein an opening through which said needle extends during use, said end being shaped to facilitate proper insertion of said needle in a patient.

10. The syringe of claim 3 or 4, wherein said protector case has, on a flat surface thereof, a data recording area.

11. The syringe of claim 3 or 4, wherein said body has a lip around said second end of a bore therein to engage a plunger, thereby preventing the accidental withdrawal thereof.

* * * * *